US007063948B1

(12) United States Patent
Soreq et al.

(10) Patent No.: US 7,063,948 B1
(45) Date of Patent: Jun. 20, 2006

(54) USES OF ANTIBODIES AGAINST ACHE AND PEPTIDES THEREOF

(75) Inventors: Hermona Soreq, Jerusalem (IL); Daniela Kaufer, Kfar Azar (IL); Alon Friedman, Gedera (IL); Shlomo Seidman, Gush Etzion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/980,263

(22) PCT Filed: May 31, 2000

(86) PCT No.: PCT/IL00/00312

§ 371 (c)(1),
(2), (4) Date: Mar. 21, 2002

(87) PCT Pub. No.: WO00/73343

PCT Pub. Date: Dec. 7, 2000

(30) Foreign Application Priority Data

May 31, 1999 (IL) .................................... 130225

(51) Int. Cl.
*G01N 17/26* (2006.01)
*C07K 16/00* (2006.01)
*C07K 5/00* (2006.01)
(52) U.S. Cl. ...................... 435/7.1; 530/387.1; 530/300
(58) Field of Classification Search ................. 435/7.1; 530/387.1, 300
See application file for complete search history.

(56) References Cited

U.S. PATENT DOCUMENTS

| 4,376,110 A | 3/1983 | David et al. |
| 5,840,479 A | 11/1998 | Little et al. |

FOREIGN PATENT DOCUMENTS

| EP | 173494 A2 | 3/1986 |
| EP | 184187 A2 | 6/1986 |
| EP | 171496 B1 | 5/1991 |
| EP | 125023 B1 | 6/1991 |
| WO | WO 86/01533 | 3/1986 |
| WO | WO 87/02671 | 5/1987 |
| WO | WO 98/22132 | 5/1998 |
| WO | WO 99/15695 | 4/1999 |

OTHER PUBLICATIONS

Boschetti, et al, 1996, Clinical Chem., 42(1): 19-23.*
Karpel, et al, 1994, Accession No. S71129.*
Li, et al, 1991, J. Biol. Chem, 266(34): 23083-23090.*
Loft, A., 1995, Danish Medical Bulletin, 42(1):54-70.*
Sternfeld, Shoham, et al, 2000, PNAS, 97(15): 8647-8652.*
Kaufer, D. and Soreq, H., 1999, Curr. Opin. Neurol., 12(6): (abstract).*
Nijholt, et al, 2004, Mol. Psychiatry, 9: 174-183.*
Magariños, et al, 1997, Proc. Natl. Acad. Sci., 94: 14002-14008.*
Ausubel, FM., Brent, R., Kingston, RE., Moore, DD., Seidman, JG., Smith, JA., Struhl, K. Current Protocols In Molecular Biology, vol. I. and II, Greene Publishing Associates and Wiley-Interscience, 1988.
Azziz-Aloya, RB., Seidman, S., Timberg, R., Sternfeld, M., Zakut, H. Expression of a human acetylcholinesterase promoter-reporter construct in developing neuromuscular junctions of *Xenopus* embryos, Proc. Natl. Acad. Sci. USA, vol. 90, pp.2471-2475, Mar. 1993.
Boschetti, N, Brodbeck, U., Jensen, SP., Koch, C., Norgaard-Pedersen, B. Monoclonal antibodies against a C-terminal peptide of human brain acetylcholinesterase distinguish between erythrocyte and brain acetylcholinesterases, Clinical Chemistry 42:1, 19-23, 1996.
Boulianne, GL., Hozumi, N., Shulman, MJ. Production of functional chimaeric mouse/human antibody, Nature vol. 312, Dec. 13, 1984.
Cabilly, S., Riggs, AD., Pande, H., Shively, JE., Holmes, WE., Rey, M., Perry, J., Wetzel, R., Heyneker, HL. Generation of antibody activity from immunoglobulin polypeptide chains produced in *Escherichia coli*, Proc. Natl. Acad. Sci. USA, vol. 81, pp. 3273-3277, Jun. 1984.
Grisaru, T, Lev-Lehman, E., Shapira, M., Chaikin, E., Lessing, JB., Eldor, A., Eckstein, F., Soreq. H. Human Osteogenesis Involves Differentiation-Dependent Increases in the Morphogenically Active 3' Alternative Splicing Variant of Acetylcholinesterase, Molecular and Cellular Biology, Jan. 1999, P. 788-795.
Guan, K., Dixon, JE. Eukaryotic Proteins Expressed in *Escherichia coli*: An Improved Thrombin Cleavage and Purification Procedure of Fusion Proteins with Glutathione S-Transferase, Analytical Biochemistry 192, 262-267, 1991.
Harlow,E., Lane, D. Antibodies, A Laboratory Manual, Cold Springs Harbor Laboratory, 1988.

(Continued)

*Primary Examiner*—Janet L. Andres
*Assistant Examiner*—Sandra Wegert
(74) *Attorney, Agent, or Firm*—Kohn & Associates, PLLC; Kenneth I. Kohn

(57) ABSTRACT

The invention relates to antibodies recognizing acetylcholinesterase or a C-terminal peptide derived from acetylcholinesterase, useful in diagnosing central nervous system (CNS) stress, elevated glucocorticoid level, disruption of the blood-brain barrier or Alzheimer's disease. The invention also relates to methods for the diagnosis of central nervous system (CNS) stress, elevated glucocorticoid level or disruption of the blood-brain barrier in a mammal, by use of the antibodies of the invention.

3 Claims, 11 Drawing Sheets

OTHER PUBLICATIONS

Kaufer, D., Friedman, A., Seidman, S., Soreq, H. Acute stress facilities long-lasting changes in cholinergic gene expression, Nature, vol. 393, May 28, 1998.

Köhler, G., Milstein, C. Continuous cultures of fused cells secreting antibody of predefined specificity, Nature, vol. 256, Aug. 7, 1975.

Loft, AG. Immunochemical determination of amniotic fluid acteycholinesterase in the antenatal diagnosis of open neutral tube defects, Danish Medical Bulletin, 42(1), 54-70, Ref: 138, Feb. 1995.

Mäder, M., Soerensen, K., Wiedman, Th., Dickman, Felgenhauer, K. Neuronal Acetycholinesterase Levels in Cerebrospinal Fluid and Serum Determined by a Specific and Sensitive Immunoassay, European Journal of Clinical Chemistry and Clinical biochemistry, 29(1) 51-55, Jan. 1991.

Morrison, SL., Johnson, MJ., Herzenberg, LA., Or VT. Chimeric human antibody molecules: Mouse antigen-binding domains with human constant region domains, Proc. Natl. Acad. Sci. USA, vol. 81, pp. 6851-6855, Nov. 1984.

Novales-Li, P., Lane, T. Isolation of Human Acetylcholinesterase from Post-Mortem Bain Tissue Samples of Alzheimer's Disease Patients and the Production of Monoclonal Antibodies, Philippine Journal of Science, vol. 124(1), 39-51, 1995.

Sambrook, J., Fritsch, EF., Maniatis, T. Molecular Cloning, A Laboratory Manual $2^{nd}$ Edition, Cold Sprongs Harbor Laboratory, 1989.

Seidman, S., Sternfeld, M., Aziz-Aloys, BR., Timberg, R., Kaufer-Nachum, D., Soreq, H. Synaptic and Epidermal Accumulations of Human Acetylcholinesterase Are Encoded by Alternative 3'-Terminal Exons, Molecular and Cellular Biology, 2993-3002, Jun. 1995.

Sternfeld, M., Patrick, JD., Soreq, H. Position effect variegations and brain-specific silencing in transgenic mice over expressing human actylcholinesterase variants, J. Physiol., Paris, 92, 249-55, 1998.

Wahl, RL., Parker, CW., Philpott, GW. Investigative Nuclear Medicine, 24, 316-325, 1983.

* cited by examiner

AD hipp
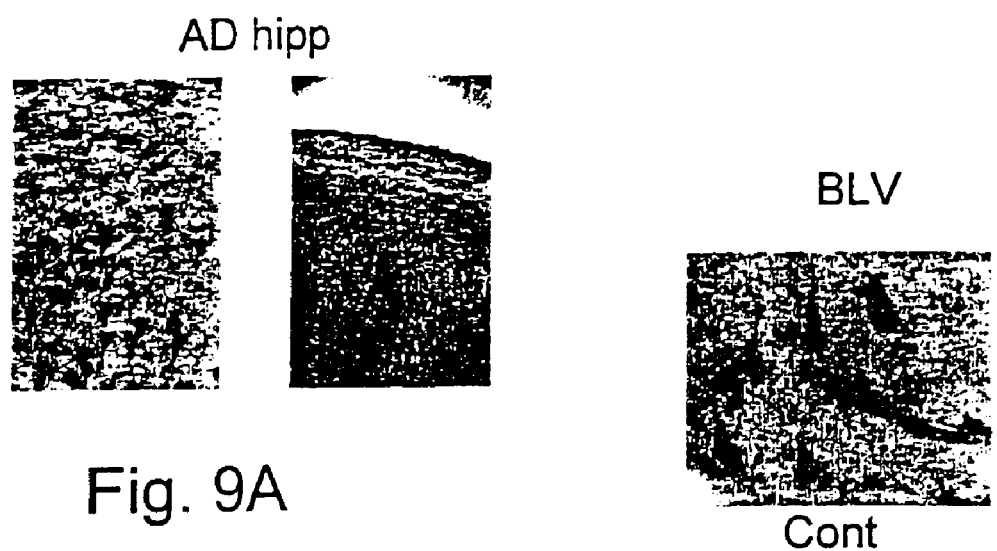
Fig. 9A
BLV
Cont
Cin -cort
Cont      AD
Fig. 9B
AD
Fig. 9C
AD
Temp-Cort
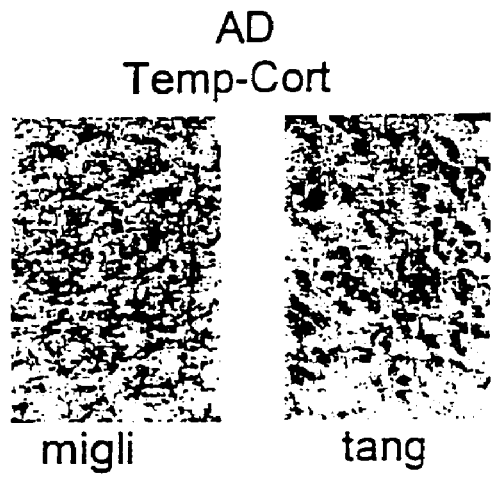
migli      tang
Fig. 9D Tem Lo (int mag)
Cont    AD Corp-Call
Cont Tem Lo (lo mag)
Cont    AD

AD

Temp-lo
Cont    AD

SEQUENCE LISTING

```
<160> NUMBER OF SEQ ID NOS: 5

<210> SEQ ID NO 1
<211> LENGTH: 26
<212> TYPE: PRT
<213> ORGANISM: Homo sapien

<400> SEQUENCE: 1

Gly Met Gln Gly Pro Ala Gly Ser Gly Trp Glu Glu Gly Ser Gly Ser
1               5                   10                  15

Pro Pro Gly Val Thr Pro Leu Phe Ser Pro
            20                  25

<210> SEQ ID NO 2
<211> LENGTH: 40
<212> TYPE: PRT
<213> ORGANISM: Homo sapien

<400> SEQUENCE: 2

Asp Thr Leu Asp Glu Ala Glu Arg Gln Trp Lys Ala Glu Phe His Arg
1               5                   10                  15

Trp Ser Ser Tyr Met Val His Trp Lys Asn Gln Phe Asp His Tyr Ser
            20                  25                  30

Lys Gln Asp Arg Cys Ser Asp Leu
        35                  40

<210> SEQ ID NO 3
<211> LENGTH: 27
<212> TYPE: PRT
<213> ORGANISM: Homo sapien

<400> SEQUENCE: 3

Phe His Arg Trp Ser Ser Tyr Met Val His Trp Lys Asn Gln Phe Asp
1               5                   10                  15
```

```
His Tyr Ser Lys Gln Asp Arg Cys Ser Asp Leu
            20                  25
```

<210> SEQ ID NO 4
<211> LENGTH: 42
<212> TYPE: DNA
<213> ORGANISM: Artificial sequence
<220> FEATURE:
<221> NAME/KEY: Artificial sequence
<222> LOCATION: (1)..(42)
<223> OTHER INFORMATION: 5' primer for intron 4 of human
      acetylcholinesterase

<400> SEQUENCE: 4
gctggatcca tcgaggggcg aggtatgcag gggccagcgg gc                    42

<210> SEQ ID NO 5
<211> LENGTH: 30
<212> TYPE: DNA
<213> ORGANISM: Artificial sequence
<220> FEATURE:
<221> NAME/KEY: Artificial sequence
<222> LOCATION: (1)..(30)
<223> OTHER INFORMATION: 3' primer for intron 4 of human
      acetylcholinesterase

<400> SEQUENCE: 5
tataagcttc taggggaga agagagggt                                    30

USES OF ANTIBODIES AGAINST ACHE AND PEPTIDES THEREOF

GRANT INFORMATION

Research in this application was supported in part by a grant from the US Army Medical Research and Material Command DAMD 17–99-9547 (July 1999–August 2004) and the Defense Advance Research Project Agency DARPA N66001-01-C-8015 (May 2001–May 2004). The U.S. Government has certain rights in the invention.

CROSS REFERENCE TO RELATED APPLICATIONS

This patent application is a National Phase Concerning a Filing Under 35 U.S.C 371, claiming the benefit of priority of PCT/IL00/00312, filed May 31, 2000, which claims the benefit of priority of Israeli Serial Number 130255, filed May 31, 1999, all of which are incorporated herein by reference.

FIELD OF THE INVENTION

The invention is directed to the field of diagnosis of a stressed condition of the central nervous system (CNS). Specifically, the invention relates to the evaluation of the levels of acetylcholinesterase and fragments thereof, for determining said stressed CNS condition. The stressed CNS condition includes penetrance of high molecular weight substances through the blood-brain barrier, and stress due to psychological, chemical and physical insults.

INTRODUCTION

The enzyme acetylcholinesterase (ACHE) is expressed in brain tissue, but also in most hematopoietic cell lineages. ACHE is expressed in many parts of the vertebrate embryo, with a developmentally regulated pattern in specific cell types and tissues during the embryonic and adult stages. ACHE diversity is noted in several pathological states, such as Alzheimer's disease, where ACHE tetramers were shown to decrease in the brain.

ACHE pre-mRNA undergoes alternative splicing. The synaptic splice variant, ACHE-S mRNA, is formed by splicing of exon 4 to exon 6. ACHE-E mRNA is formed by splicing of exon 4 to exon 5. AChE-R mRNA is formed by lack of splicing of pseudointron 4, yielding the E1-E2-E3-E4-I4-E5 mRNA transcript.

It has more been surprisingly found that ACHE-R mRNA, and the ACHE-R protein, are elevated in response to CNS insults. These insults include psychological, chemical, and physical insults. It has further been found that the blood-brain barrier is disrupted following stress insults, and that occurrence of said ACHE-R protein in fluids of the central nervous system may serve as an indicator of central nervous system stress and of disruption of the blood-brain barrier.

SUMMARY OF THE INVENTION

This invention relates to an antibody recognizing "readthrough" acetylcholinesterase or more specifically a C-terminal peptide derived from acetylcholinesterase, for use in diagnosing central nervous system (CNS) stress, elevated glucocorticoid level, or disruption of the blood-brain barrier. The CNS stress is preferably CNS stress caused by psychological, chemical, or physical insult. The antibody preferably recognizes a C-terminal peptide derived from Acetylcholinesterase. The C-terminal peptide is preferably a peptide having the amino acid sequence as denoted by SEQ ID: No. 1, 2, or 3. Further preferably, the antibody is monoclonal.

The invention also provides a method for the diagnosis of central nervous system (CNS) stress, elevated glucocorticoid level, or disruption of the blood-brain barrier in a mammal, comprising obtaining a sample from said mammal, contacting said sample with an antibody of the invention, removing unbound antibody, and detecting the extent of reaction between said antibody and acetylcholinesterase or a fragment thereof present in said sample. The said CNS stress is preferably CNS stress caused by physical, chemical, or psychological insult. In a preferred embodiment of the invention, the physical insult is head injury, head trauma, or exposure to irradiation. In a further preferred embodiment of the invention, the chemical insult is exposure to insecticide of nerve gas.

In a preferred embodiment the invention relates to a method for the diagnosis of Alzheimer's disease, comprising obtaining a sample from a subject, contacting said sample with an antibody of the invention, removing unbound antibody, and detecting the extent of reaction between said antibody and acetylcholinesterase or a fragment thereof present in said sample.

The sample is preferably a serum or cerebrospinal fluid sample.

Human cerebrospinal fluid (CSF) samples from stressed (+) or non-stressed (−) subjects were subjected to SDS-PAGE. The blots were incubated with antibodies against the common domain of AChE (corn Abs) (left), or with anti-ARP antibodies (α-I4) (right). Xenopus oocytes (I4) extracts (ext) and recombinant AChE-S (rE6) served as controls.

Figure 2A:
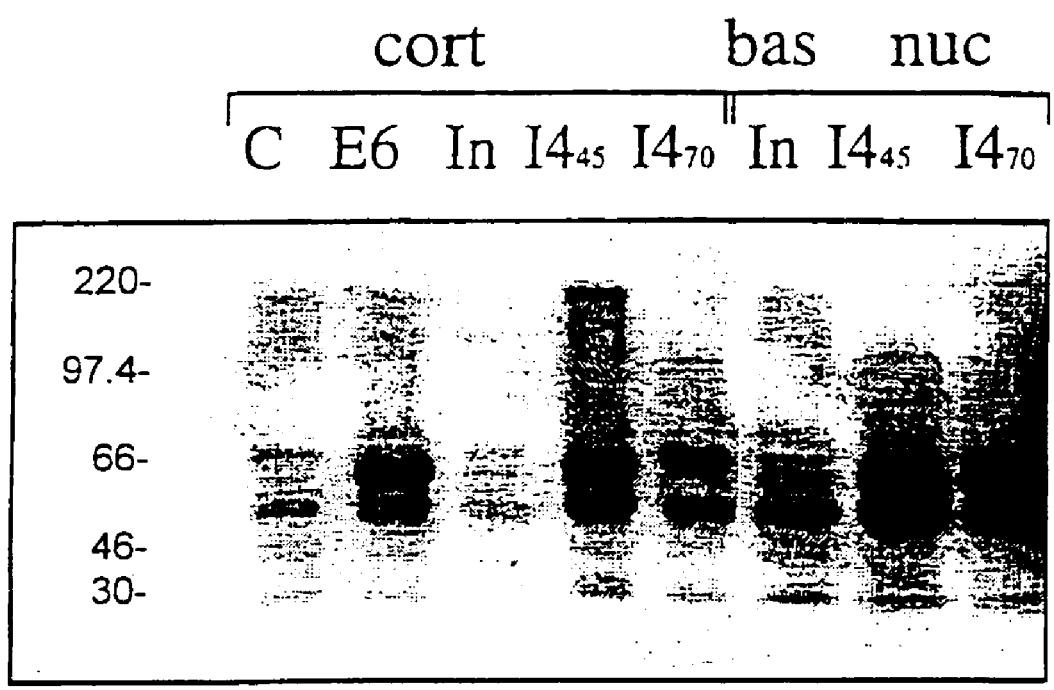
Figure 2B:
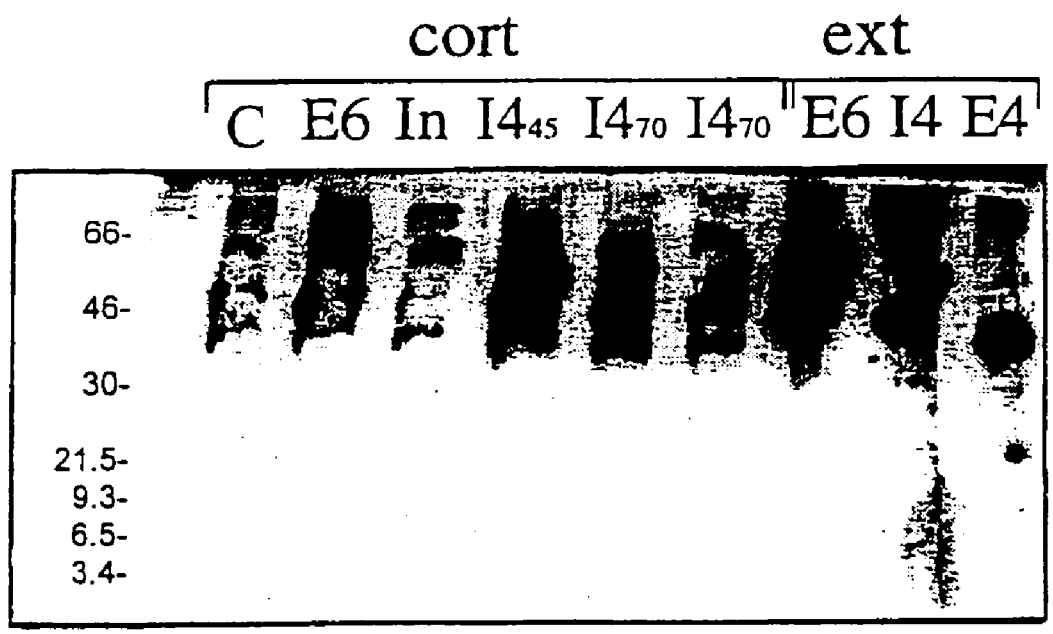

FIGS. 2A and 2B—Detection of AChE in brain tissues of transgenic mice expressing Human AChE constructs FIG. 2A-*shows* Western blot analysis of extracts from the cortex (cort) and basal nuclei (bas nuc) region obtained from the brain of control (C) and transgenic FVB/N mouse, expressing human ACHE variants, E6 expressing human ACHE-S, "In" designates a transgenic mouse expressing insertion-inactivated human ACHE-S, I4$_{45}$ and I4$_{70}$A denote transgenic mice expressing various ACHE-R constructs. The tissues were extracted, run on 8% SDS-PAGE gels and blotted using antibodies to common domain. As a control, extracts (ext) from *Xenopus* oocytes expressing human ACHE-S (E6), ACHE-R (I4), or ACHE-E (E4) were run in parallel.

FIG. 2B-*shows* Western blot analysis of the similar samples that were separated on 4–20% gradient SDS-PAGE gel and blotted using antibodies to GST-I4.

Figure 3:
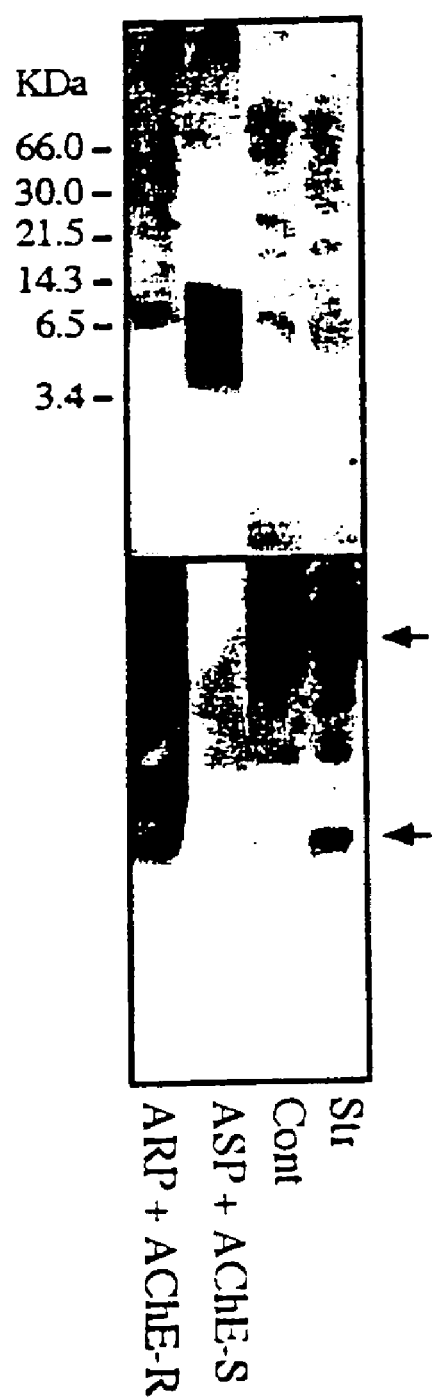

FIG. 3-ARP accumulates in the serum under stress

Poinceau-stained polyacrylamide gradient gels (4–20%) (Top), that were loaded with protein extract from COS cells transfected with ACHE-R encoding plasmid and mixed with synthetic ARP (ARP+AChE-R); recombinant ACHE-S (Sigma), mixed with synthetic ASP (ASP+AChE-S); serum (2 μL) from a saline-injected mouse, removed 24 hr post-treatment as control (cont); serum from a mouse subjected stress (Str). Molecular weight markers (kdA) are shown on the left. The gel was then blotted and incubated with affinity-purified rabbit antibodies elicited toward a recombinant GST-ARP (Bottom).

Figure 4:
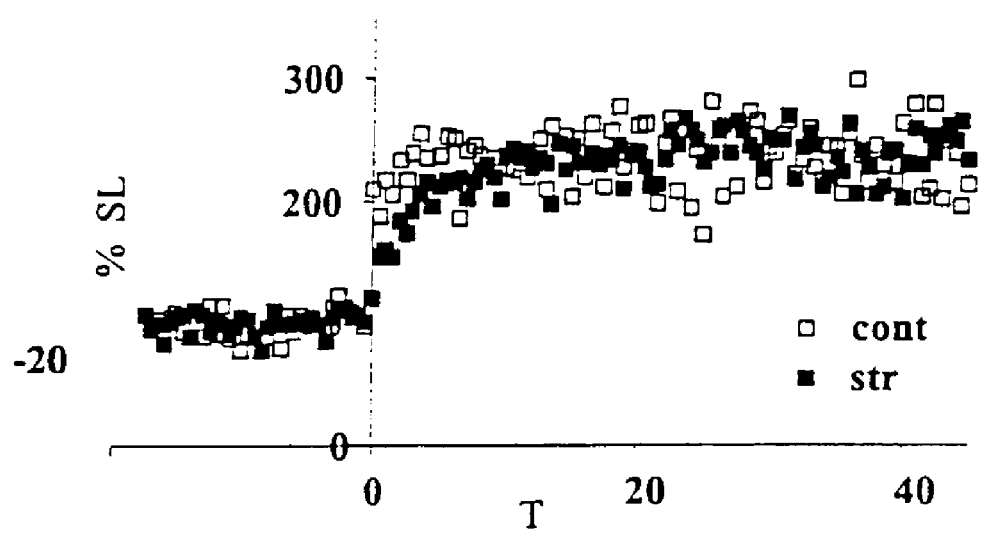

FIG. 4—Confined swim stress induces within 1 hr subtle delay in LTP induction

Schaffer collaterals-CA1 synaptic pathway on hippocampal slices from a stressed (str) vs. control (cont) mice were tested after LTP induction. The changes in the slope (sl) of the post synaptic field potential were followed for 3 hrs (indicated by Time=T in minutes).

Figure 5:
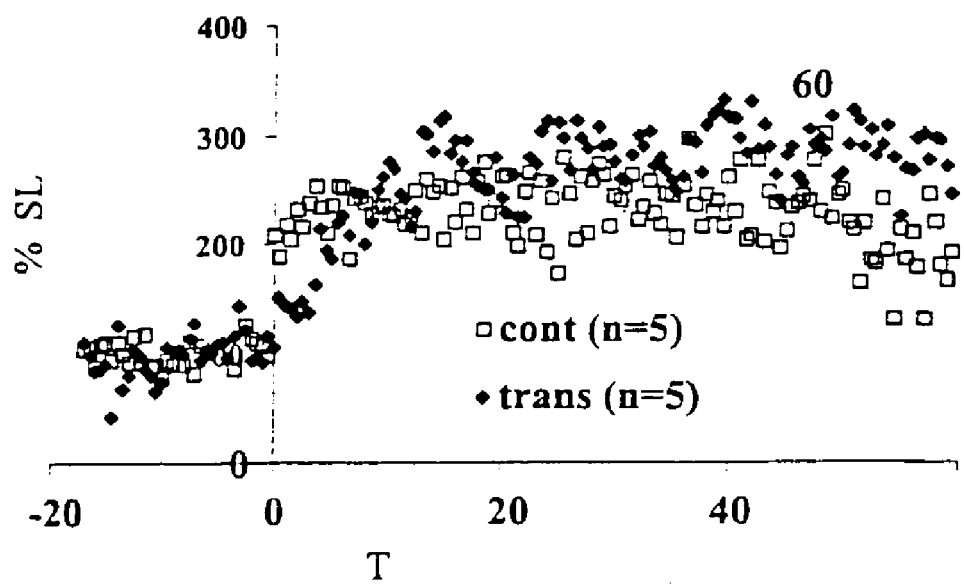

FIG. 5—Slices from transgenics over-expressing AChE-R also display slow onset of LTP Schaffer collaterals-CA1 synaptic pathway on hippocampal slices from a transgenic mice over-expressing the "readthrough" isoform ACHE-R (trans) vs. control (cont) mice were tested after LTP induction. The changes in the slope (sl) of the post synaptic field potential was followed for 3 hrs (indicated by Time=T in minutes).

Figure 6B:
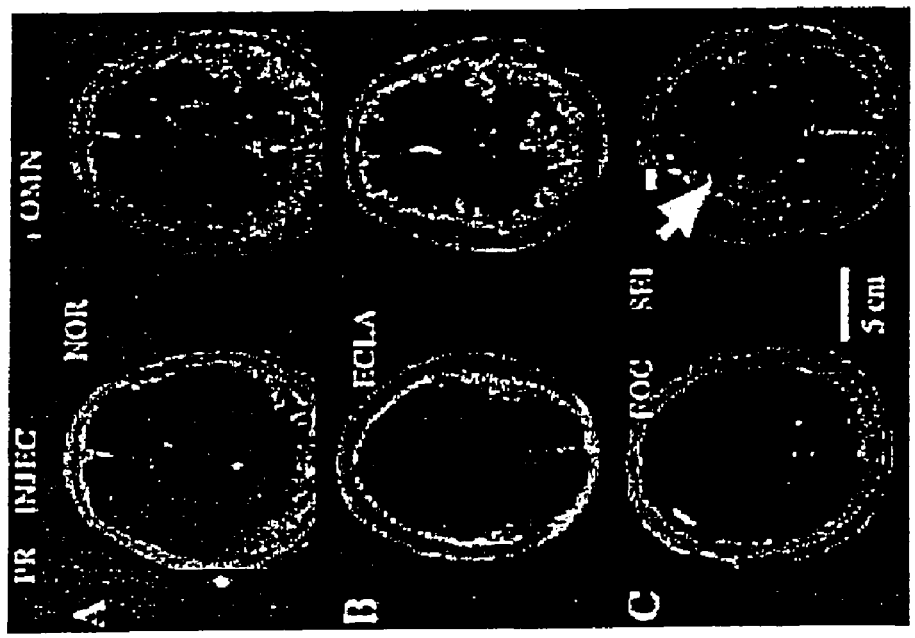
Figure 6A:
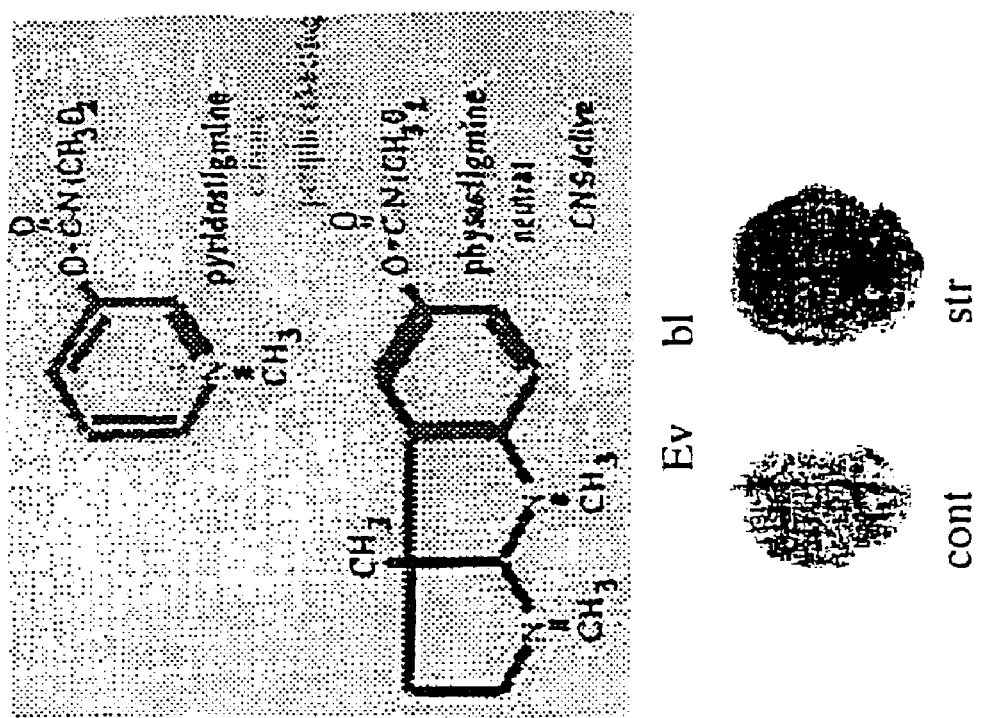
Figure 6C:
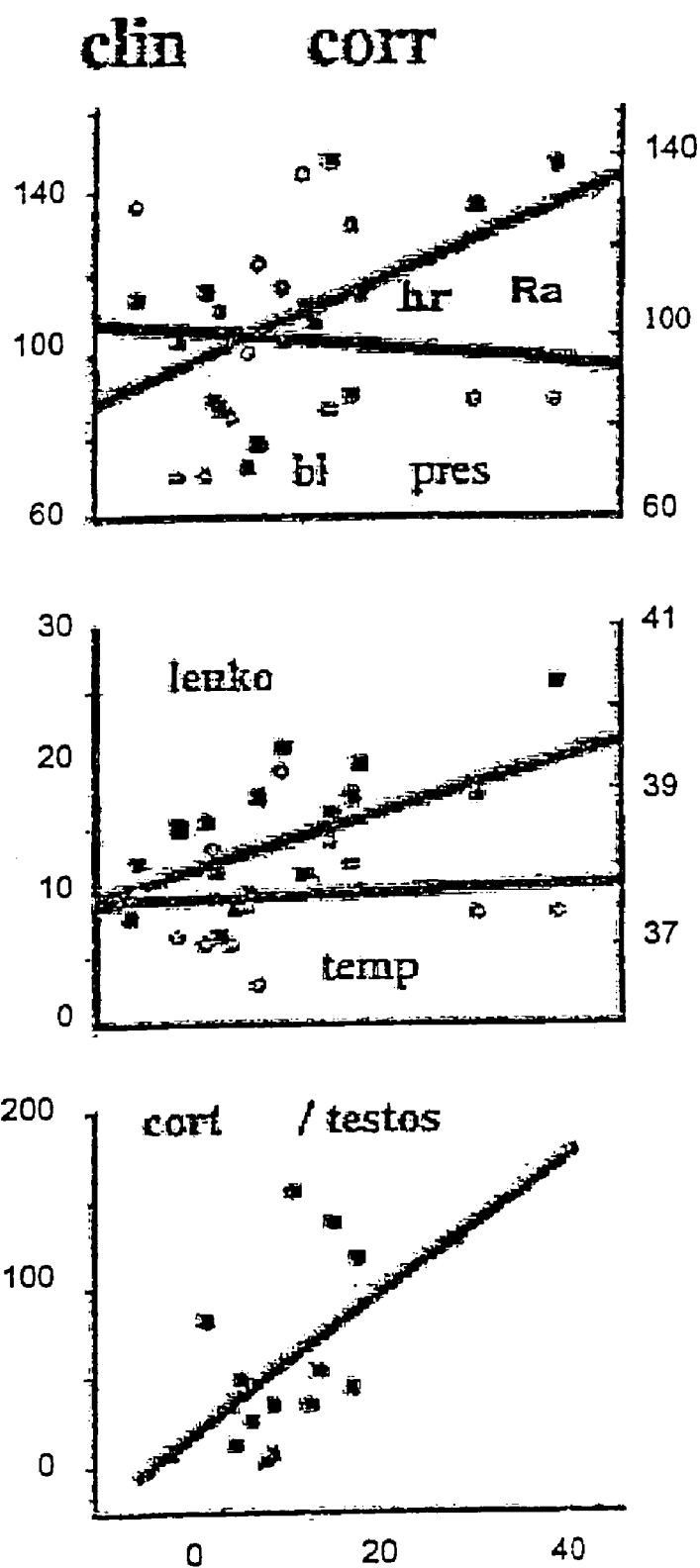

FIGS. 6A to 6C—Blood-Brain Barrier penetrance under stress

FIG. 6A-shows dye penetration to the brain of stressed mice (str), as compared to non-stressed control mice (cont).

FIG. 6B-shows Computerized Tomography scans of patients with (OMN) and without (PR INJEC=pre injection), administration of Omnipaque (Nycomed AS), a soluble iodine containing contrast agent. The samples are as follows: NOR (normal), ECLA (eclampsia) and FOC SE (focal seizure).

FIG. 6C-shows clinical correlation (cin corr) of BBB with stress indicators such as heart rate (hr ra), leukocyte (leuk) number, and serum cortisol (cort) and testosterone (testos) levels, blood pressure (bl pres) and body temperature (temp).

Figure 7A:
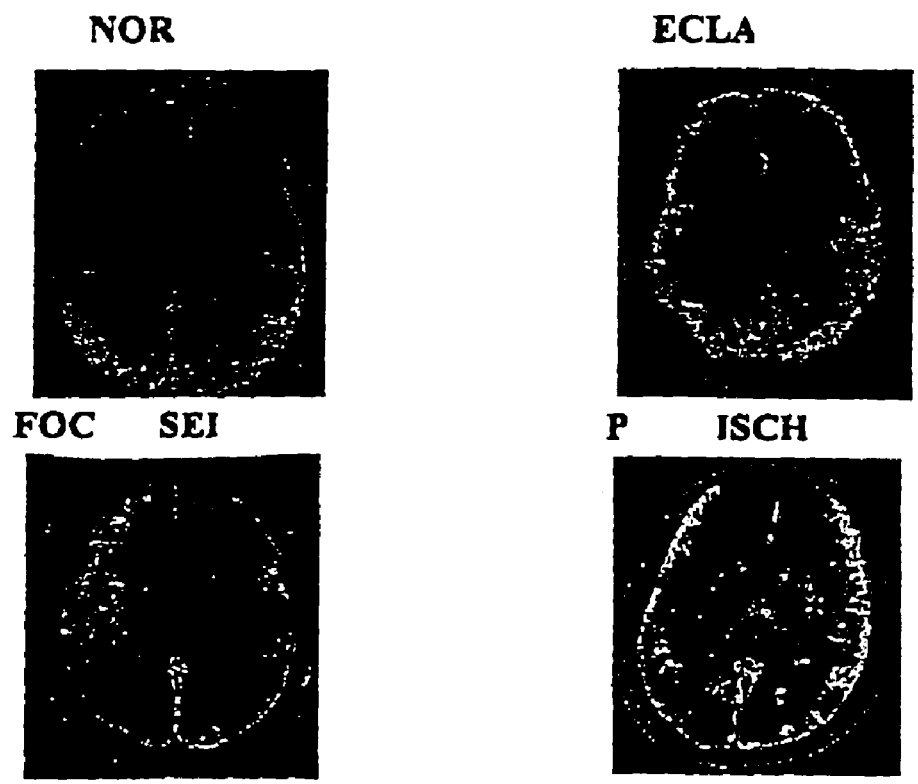
Figure 7B:
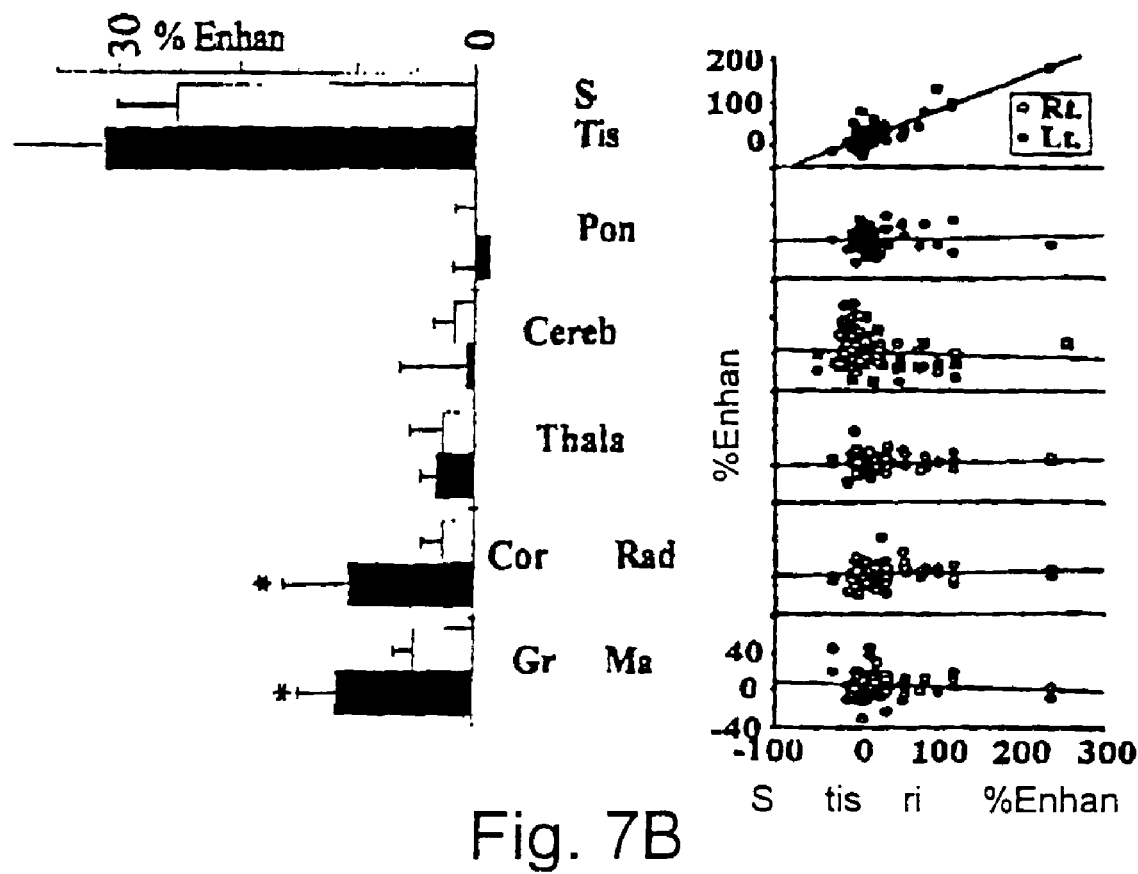

FIGS. 7A and 7B—CT scans of patients and statistical analysis of regions displaying enhanced signal therein FIG. 7A-shows an example of enhanced Omnipaque signal revealed by CT scan of Eclampsia (ECLA), Focal Seizure (FOC SE) versus control patients (NOR), and also in post-ischemia patients (PO ISCH).

FIG. 7B-shows analysis for the region of the brain showing greatest signal enhancement Enhanc), significant signal enhancement was found in the Corona Radiata (Cor Rad), Gray matter (Gr Ma), and soft tissue (S. Tis) regions. Very little enhancement of penetration of contrast agent into the Thalamus (Thal) region was found, and the Cerebellum (Cereb) and Pons (Pon) regions appeared unaffected.

Figure 8A:
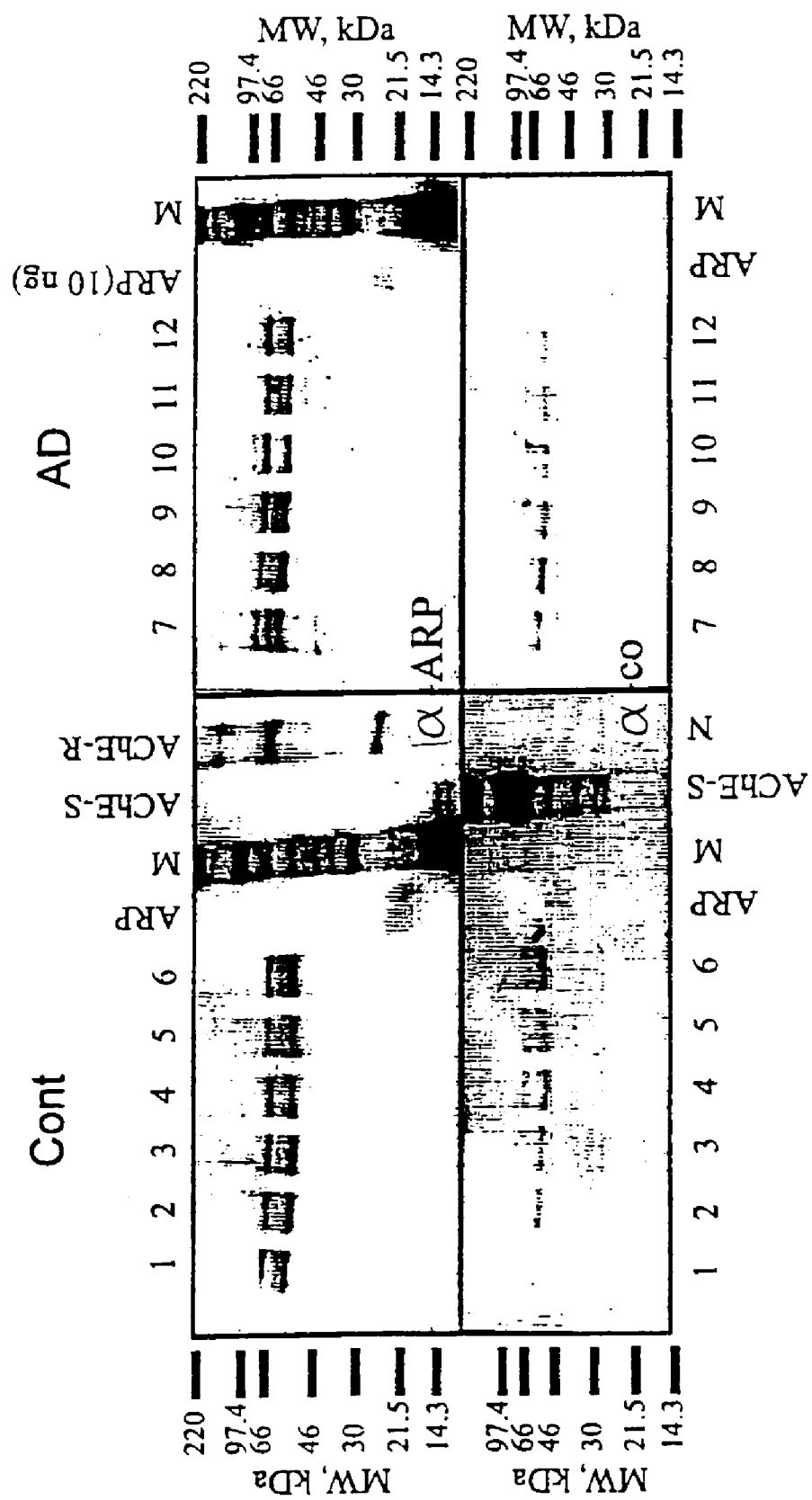

FIG. 8A and FIG. 5B-Expression of A ChE in AD patients

FIG. 8A-shows immunodetection of AChE in AD and control CSF. CSF samples from Alzheimer's disease patients (AD) or from healthy controls (coot) were subjected to electrophoretic separation followed by immunoblot analysis. Blots were incubated with antibody against the C-terminal peptide unique to ACHE-R (a-ARP— top panel), or with the antibody targeted to the common domain to all AChE isoforms (a-cor; bottom panel). ARP, human recombinant ACHE-S and ACHE-R were used as positive or negative controls on right of the filters. The molecular weight markers are indicated by M.

Figure 8B:
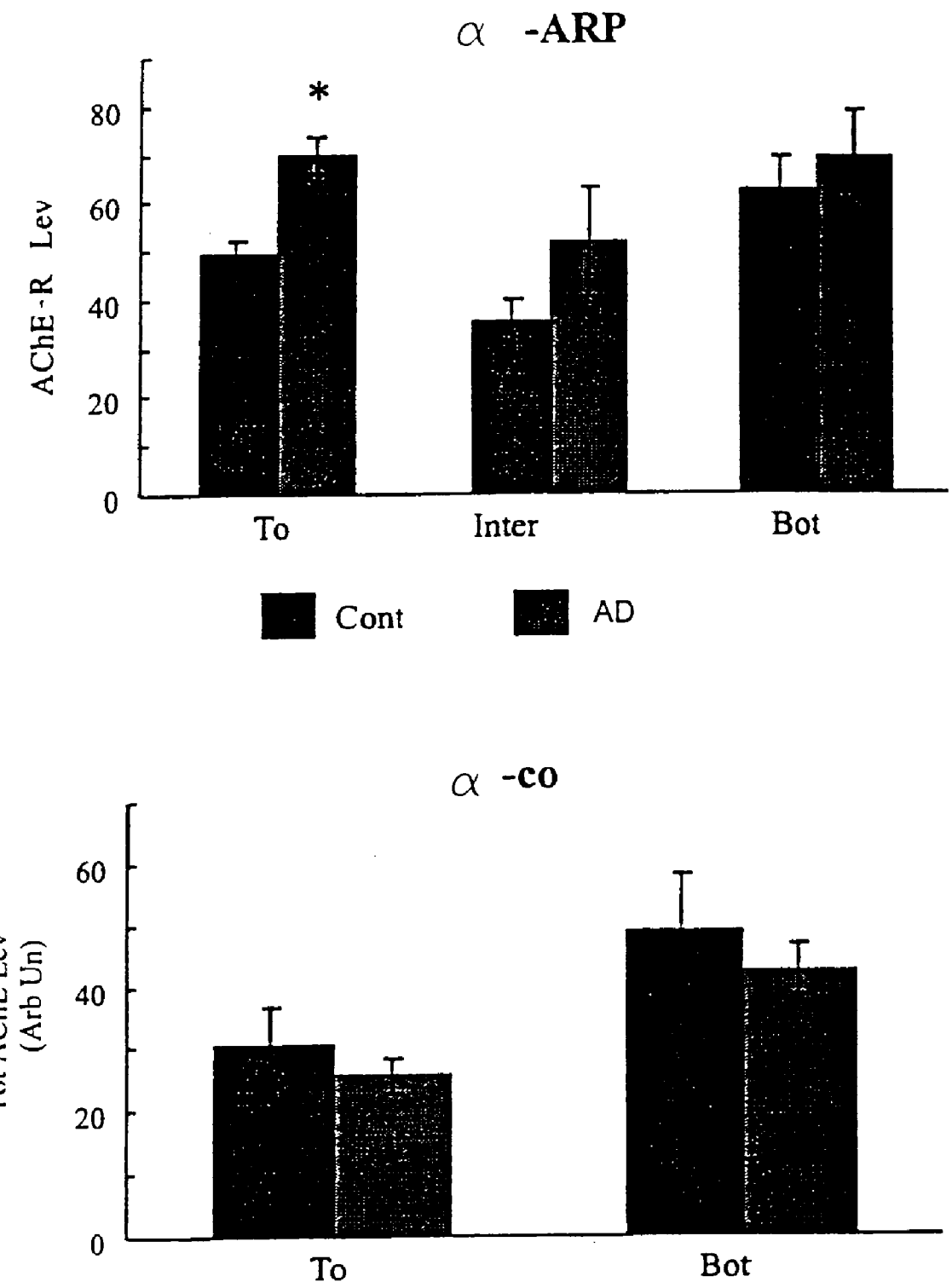

FIG. 8B-shows quantitation of the immunodetection signals by densitometric analysis. AChE-R (left) and total AChE (right) protein levels (Tot AChE Lev) are presented in terms of relative intensities of each band within individual lanes of the FIG. 8A filters, after incubation with anti-ARP (a-ARP) and anti-core (a-co) respectively. Three proteins are observed with anti-ARP [Top (To), Intermediate (Inter) and Bottom (Bot)], but only two with anti-core (top and bottom). Values reported are mean ± SEM averaged from six independent determinations. *$p<0.05$, significantly different from group as assessed by Student's test.

FIGS. 9A to 9H—Immunolabeling of ARP in normal vs. AD human brain sections

FIG. 9A—shows Alzheimer's Disease hippocampus (designated AD-hipp) paraffin embedded sections. Neurons (Left) and microglial cells (Right) are stained in the same region.

FIG. 9B—shows control (cont, Left) and Alzheimer's Disease (AD, Right) cingulate cortex (Cin-cort) paraffin embedded sections. Blood vessels in the control sections are strongly stained.

FIG. 9C—shows staining of blood vessels (Blv) in control (cont, Top) and Alzheimer's Disease (AD, Bottom) cingulate cortex paraffin embedded sections. In the control sections blood vessels are strongly stained.

FIG. 9D—shows Alzheimer's Disease (AD) temporal cortex (Temp-cort) paraffin embedded sections. Both microglial (migli, Left) and tangle cells (tang, Right) are strongly stained.

Figure 9E:
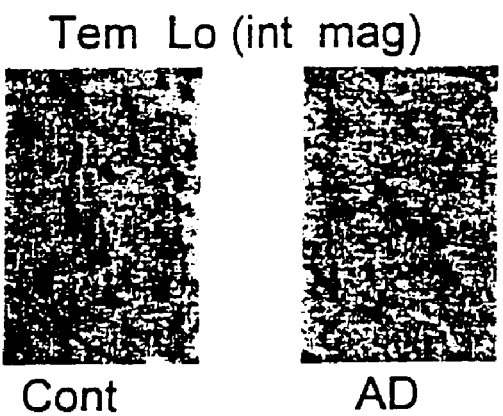

FIG. 9E—shows an intermediate magnification (int mag) of control (cont, Left) and Alzheimer's Disease (AD, Right) temporal lobe (Temp-lo) paraffin embedded sections. In the normal control sections only pyramidal neurons are stained. In the AD sections note the staining of microglial cells, absent from the control.

Figure 9F:
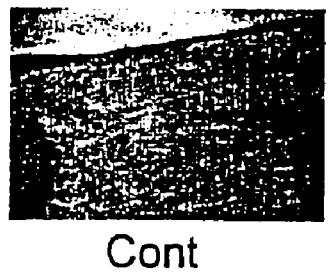
Figure 9F:
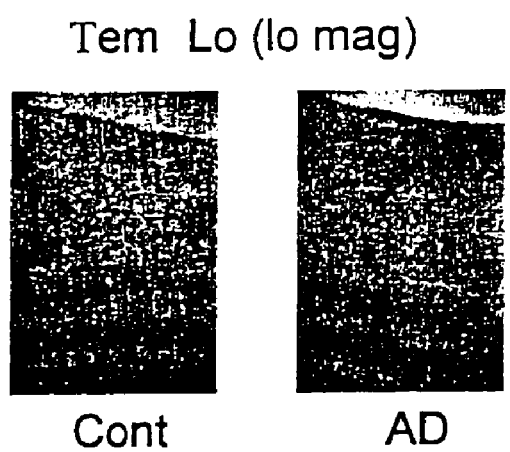

FIG. 9F—shows a low magnification (lo mag) of FIG. 9E. In the normal control sections (Left) staining appears in layers, while microglial cells appears in the AD sections (Right).

Figure 9G:

FIG. 9G—shows staining of control (cont, Top) and Alzheimer's Disease (AD, Right) Corpus callosum (Corp-call) paraffin embedded sections. Note the staining along neuronal extension in the AD sections.

Figure 9H:
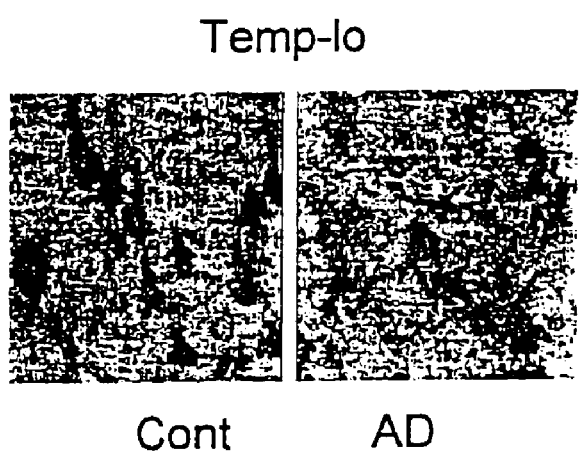

FIG. 9H—shows ARP staining of neurons and microglia in normal control (cont, Left) and Alzheimer's Disease (AD, Right) temporal lobe (Temp-lo) paraffin embedded sections. In the normal control sections neurons and blood vessels are stained, while in the AD sections microglial cells are stained.

DETAILED DESCRIPTION OF THE INVENTION

A number of terms as used herein are defined hereinbelow:

ACHE, Acetylcholinesterase;
ARP, acetylcholinesterase "readthrough" peptide,
ASP, acetylcholinesterase "synaptic" peptide;
BuChE, Butyrylcholinesterase;
CNS, central nervous system;
common domain, the region of AChE which is common to all splice variants, includes exons 1–4;
CSF, cerebrospinal fluid;
GST, glutathione-5-transferase;
ODN, oligodeoxynucleotide;
ORF, open reading frame;
RT, room temperature;
UTR, untranslated terminal region;
WBC, white blood cells.

A number of methods of the art of molecular biology are not detailed herein, as they are well known to the person of skill in the art. Such methods include site-directed mutagenesis, PCR cloning, expression of cDNAs, analysis of recombinant proteins or peptides, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN:

047150338X, John Wiley & Sons, Inc. 1988, and Short Protocols in Molecular Biology, by F. M. Ausubel et al. (eds.) 3rd ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al. (eds), John Wiley & Sons. Inc., New York, N.Y.

The invention comprises anti-AChE antibodies and the use thereof for the diagnosis of pathological conditions of the CNS. Polyclonal antibodies may be generated in rabbits, chicken, mice, rats, sheep, or similar mammals. For generation of antibodies against a peptide of the invention, the peptide is produced by recombinant DNA technology in mammalian cells, as described in the above general references for molecular biology. Alternatively, the peptide may be synthetically produced by organic chemistry. The peptide may also be produced in bacterial or insect cells as detailed in the above-noted Current Protocols in Molecular Biology, Chapter 16.

The peptide is purified from the cells in which it has been produced. Peptide purification methods are known to the person of skill in the art and are detailed e.g., in the above-noted Current Protocols in Molecular Biology, Chapter 16, and in Current Protocols in Protein Science, Wiley and Sons Inc. Chapters 5 and 6. Advantageously, the peptide may be produced as a fusion with a second protein, such as Glutathione-5-transferase or the like, or a sequence tag, such as the histidine tag sequence. The use of fusion or tagged proteins simplifies the purification procedure, as detailed in the above-noted Current Protocols in Molecular Biology, Chapter 16, and in the instructions for the his-tag protein expression and purification kit, as available from Qiagen GrnbH, 40724 Hilden, Germany.

If the protein or peptide has been expressed as a fusion protein, it may be desirable to cleave the fusion partner before using the protein for the generation of antibodies, in order to avoid generation of antibodies against the fusion partner. The cleavage of fusion partners and the isolation of the desired protein is described in the above-noted Current Protocols in molecular Biology, Chapter 16. Vectors, protocols and reagents for expressing and purifying maltose-binding protein fused recombinant proteins are also available commercially.

When producing a peptide of the invention, it may be desirable not to remove the fusion partner, as the fusion protein may stimulate the production of antibodies against the peptide. Generally, this consideration may be relevant when generating antibodies from peptides that are less than 50 amino acids in length. In particular, it has been found that the ARP peptide, when injected, is virtually non-immunogenic. A Keyhole Limpet hemocyanin (KLH)-conjugated ARP peptide was found to elicit antibodies unable to detect ARP or acetylcholinesterase. Antibodies capable of detecting ARP were successfully generated using a Glutathione-S-transferase-ARP fusion protein (detailed hereinbelow). Accordingly, in a preferred embodiment of the invention, antibodies are elicited using a conjugate or fusion protein of the peptide of the invention as antigen. A preferred fusion partner is Glutathione-S-transferase.

As noted further above, the peptide may also be synthesized by chemical methods known in the art of chemistry.

The generation of polyclonal antibodies against proteins is described in Chapter 2 of Current Protocols in Immunology, Wiley and Sons Inc. The generation of antibodies against peptides may necessitate some changes in protocol, because of the generally lower antigenicity of peptides when compared to proteins. The generation of polyclonal antibodies against peptides is described in the above-noted Current Protocols in Immunology, Chapter 9, and exemplified hereinbelow.

Monoclonal antibodies may be prepared from B cells taken from the spleen or lymphnodes of immunized animals, in particular rats or mice, by fusion with immortalized B cells under conditions which favor the growth of hybrid cells. For fusion of murine B cells, the cell line Ag-8 is preferred.

The technique of generating monoclonal antibodies is described in many articles and textbooks, such as the above-noted Chapter 2 of Current Protocols in Immunology. Chapter 9 therein describes the immunization, with peptides, of animals. Spleen or lymphnode cells of these animals may be used in the same way as spleen or lymphnode cells of protein-immunized animals, for the generation of monoclonal antibodies as described in Chapter 2 therein.

The techniques used in generating monoclonal antibodies are further described in Kohler and Milstein, Nature 256, 495497, 1975 and in U.S. Pat. No. 4,376,110.

In the preparation of antibodies from a gene bank of human antibodies the hypervariable regions thereof are replaced by almost random sequences, is described in U.S. Pat. No. 5,840,479. This method of antibody generation is preferred if it is difficult to immunize an animal with a given peptide or protein. The peptide of the invention may be poorly immunogenic, even as a conjugate. The antibodies described in U.S. Pat. No. 5,840,479 are further preferred if it is desired to use antibodies with a structure similar to human antibodies, for instance, when antibodies are desired that have low immunogenicity in humans.

Once a suitable antibody has been identified, it may be desired to change the properties thereof. For instance, a chimeric antibody may achieve higher yields in production. Chimeric antibodies wherein the constant regions are replaced with constant regions of human antibodies are further desired when it is desired that the antibody be of low immunogenicity in humans. The generation of chimeric antibodies is described in a number of publications, such as Cabilly et al., Proc. Natl. Acad. Sci. USA 81, 3273, 1984, Morrison et al., Proc. Natl. Acad. Sci. USA 81, 6851, 1984, Boulianne et al, Nature 312, 643, 1984, EP 125023, EP 171496, EP 173494, EP 184187, WO 86/01533, WO 87/02671, and Harlow and Lane, Antibodies: A Laboratory Manual, Cold Spring harbor Laboratory, 1988.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24, 316–325, 1983).

It will be appreciated that Fab and F(ab')$_2$ and other fragments of the antibodies useful in the present invention may be used for the detection and quantitation of the peptide of the invention and of intact ACHE or its isoforms, according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody, that can also be recognized by that antibody. Epitopes or "antigenic determinants" usually consist of chemically active surface groupings of molecules such as amino acids or sugar side chains, and have specific three-dimensional structural characteristics as well as specific charge characteristics.

An "antigen" is a molecule or a portion of a molecule capable of being bound by an antibody, which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention, may be used to quantitatively or qualitatively detect the peptide of the invention, in a sample. This can be accomplished by immunofluorescence techniques employing a fluorescent or color-labeled antibody (see below) coupled with light microscopic, flow cytometric, or fluorometric detection. The antibodies (or fragments thereof) useful in the present invention may be employed histologically, as in immunofluorescence or immunoelectron microscopy, for in situ detection of a peptide of the invention. In situ detection may be accomplished by removing a histological specimen from a mammal, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the peptide, but also its distribution on the examined tissue. Using the present invention, those of ordinary skill will readily perceive that any of wide variety of histological methods (such as staining procedures) can be modified in order to achieve such in situ detection.

Such assays for the protein of the invention typically comprise incubating a biological sample, such as a biological fluid, a tissue extract, freshly harvested cells such as lymphocytes or leukocytes, or cells which have been incubated in tissue culture, in the presence of a labeled antibody capable of identifying the peptide, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect receptor tyrosine phosphatase (R-PTPase) through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The present invention provides an immunoassay for the detection and quantification of a peptide of the invention. The creation of immunoassays, such as RIA or ELISA, has been described in many articles, textbooks, and other publications. Reference is made to WO 97/03998, p. 4, line 4 to p. 52, line 27. Immunoassays of the invention may be if two general types: Firstly, immunoassays using an immobilized peptide of the invention, may be used. Secondly, immunoassays using immobilized antibodies directed against an epitope of a peptide of the invention may be used to quantify a peptide of the invention. In a preferred embodiment of the invention, the assay is an immunoblot assay. The sample, e.g., a cerebrospinal fluid (CSF) sample, is diluted, e.g., 1:10, in order to avoid overloading. The sample is then loaded onto a polyacrylamide gel, optionally a gradient gel, and electrophoresed. Synthetic or recombinantly produced peptide preferably SEQ ID: No. 1, SEQ ID: No. 2, or SEQ D: No. 3, may be added in separate lanes or spiked to the sample lanes, as positive controls. The gel is then blotted, preferably onto a Nitrocellulose or Nylon membrane. The blot is reacted with antibodies against the acetylcholine-derived peptide, preferably antibodies reactive with SEQ ID: No. 1, 2 or 3. A more preferred antibody is the rabbit anti-GST-ARP antibody as described herein. Bound antibody may then be detected by antibodies reactive with the antibody of the invention, e.g., anti-rabbit immunoglobulins. These immunoglobulins are preferably labeled, e.g., by Peroxidase conjugation. The detection of the label is then carried out according to methods known in then art. Preferably, peroxidase-conjugated immunoglobulins are detected using the ECL™ detection system (Amersham Pharmacia Biotech, UK).

As described above, a preferred sample is serum. However, other body fluids may be used, including cerebrospinal fluid, liquor, saliva, and the like. Also liquid extracts of body tissue may be analyzed. Alternatively, body tissue may be analyzed without extraction using cytochemical staining or immunostaining as described herein.

A preferred body fluid is cerebrospinal fluid. For instance, increased levels of ACHE or of a peptide of the invention in cerebrospinal fluid, may be indicative of elevated blood cortisol levels, and may further be indicative of stress.

Such assays as hereinabove described may find use in diagnostics, as the level of the peptide of the invention may need to be evaluated in a number of conditions. For instance, such assays may be useful in order to monitor the effect of treatment of a patient with a peptide of the invention. Furthermore, such assays may be used in determining stress due to psychological, chemical, or physical insult to the CNS (see Examples hereinbelow).

Thus, in a preferred embodiment, the invention provides a method for the diagnosis of psychological, chemical, or physical insult to the CNS, comprising obtaining a sample from said mammal, contacting said sample with an antibody of the invention, removing unbound antibody, and detecting the extent of reaction between said antibody and acetylcholinesterase or a fragment thereof present in said sample. The sample is preferably cerebrospinal fluid.

In a specifically preferred embodiment the invention relates to a method for the diagnosis of Alzheimer's disease in a subject comprising obtaining a sample from said subject, contacting said sample with an antibody of the invention, removing unbound antibody, and detecting the extent of reaction between said antibody and acetylcholinesterase or a fragment thereof present in said sample.

EXPERIMENTAL PROCEDURES

In situ hebridization: In situ hybridization procedures, were performed on cultured cells and tissues, as detailed elsewhere (Grisaru et al., Mol. Cell. Biol. 19, 788–95, 1999, Kaufer et al., Nature 393, 373–7, 1998). Cultured cells were centrifuged at 300×g and fixed, using 4% paraformaldehyde, to collagen-coated cover slips placed on the bottom of the culture well. 5'-Biotinylated, 2'-O-methylated AChEcRNA probes complementary to 3'-alternative human ACHE exons were employed. Detection and quantification of the various AChEmRNA transcripts in fetal tissues were performed as previously described (Grisaru et al., ibid). Confocal microscopy scans of the culture-derived cells were obtained using a MRC-1024 Bio-Rad confocal microscope (Hemel Hempstead Herts, UK). A projection was built from each cell image and specific criteria were set for size and intensity of the Fast Red fluorescence. Image-Pro 3.0 software (Media Cybernetics, Silver Spring, Md., USA) was used to analyze the signals obtained. ANOVA (Analysis of Variance) test was used for calculation of p values.

Immunoblot: Mouse serum was diluted 1:10. ARP, ASP, recombinant ACHE-S (Sigma Chemical Co.) and recombinant ACHE-R extracted from transfected COS cells (Ben Aziz-Aloya et al., Proc. Natl. Acad. Sci. USA 90, 2471–5, 1993, Seidman et al., Mol. Cell. Biol. 15, 2993–3002, 1995) served as positive controls. Protein electrophoresis in SDS gradient (4–20%) polyacrylamide gels (Bio-Rad Laboratories, Hercules, Calif.) was followed by immunodetection using the rabbit anti-GST-ARP antibodies, Peroxidase-conjugated anti-rabbit immunoglobulins and ECL™ detection (Amersham Pharmacia Biotech, UK).

Animal models and in vivo experiments: Transgenic FVB/N mouse pedigrees expressing human ACHE variants were described elsewhere, as were the biochemical methods for measuring ACHE activity (Sternfeld et al., J. Physiol., Paris, 92, 249–55, 1998). The confined swim protocol for exerting acute psychological stress was performed as detailed (Kaufer et al., Nature 393, 373–7, 1998). Immediately following the stress, the treated mice were injected intraperitoneally with 0.03 ng AS1 (AS1 is a 2'-O-methyl-protected antisense oligodeoxynucleotide targeted to ACHE exon 2, which is common for AChE-S and ACHE-R mRNA). per gram body weight. Another group of non-stressed mice were injected with normal saline. Twenty-four hours later, the animals were sacrificed and peripheral blood was collected in EDTA covered tubes (Becton Dickinson Immunocytochemistry System, Inc., San lose, CA) prepared with 25 units of heparin sodium USP (Kamada LTD, Kibbutz Beit-Kama, Israel). Whole blood AChE activity was analyzed, and WBC and platelet counts determined, using an Ac-T diff hematology analyzer (Beckman Coulter, Inc., Fullerton, Calif.).

EXAMPLE 1

Expression of Recombinant ARP

The sequence coding the C-terminal region of I4 (i.e., the "readthrough" variant of acetylcholinesterase, comprising the ARP peptide sequence), was amplified by PCR using the following oligonucleotide primers:

GCT GGA TCC ATC GAG GGG CGA GGT ATG CAG GGG CCA GCG GGC (I4-up), also denoted as SEQ ID: No. 4, and TAT AAG CTT CTA GGG GGA GAA GAG AGG GG' (I4-down), also denoted as SEQ ID: No. 5, and introduced into pGEX-KG (ATCC Accession No. ATCC77103, see also Anal. Biochem. 192:262–267, 1991) plasmid.

Antibody Production

GST and I4-GST fusion protein were purified from the supernatant of E. coli lysate by affinity chromatography on glutathione-Sepharose (Pharmacia), eluted with 10 mM reduced glutathione in 50 mM Tris-HCl, pH 8.0, dialyzed to 0.1 M ammonium acetate buffer, pH 7.0, aliquoted and lyophilized. The stability and identity of the protein was confirmed by SDS-PAGE. The following protease inhibitors were used during the preparation: aprotinin (10 µg/ml), benzamidine (5 mM), Pefabloc SC (0.2 mM), and EDTA (1 mM). Prior to affinity chromatography, the E. coli lysate was incubated for 20 min at 37° C. with 0.2 mM Mg-ATP in order to dissociate the fusion proteins from contamination of bacterial proteins. The procedure was performed according to Pharmacia recommendations.

Two New Zealand female rabbits were immunized subcutaneously with 0.3 mg fusion protein in complete Freund's adjuvant, and then reimmunized monthly with 0.2 mg fusion protein in incomplete Freund's adjuvant. Blood samples were taken 10 days after the immunization. The specific antibodies in the sera were detected by ELISA on immobilized fusion protein, in the presence of excess of soluble GST (20 µg/ml). The reacting sera were chosen for antibody purification. The immobilized I4-GST, GST and E. coli lysate were prepared using Affigel 10 (Bio-Rad) according to the manufacturer's recommendations.

Crud IgG fraction was prepared from the serum by 50% saturation $(NH_4)_2SO_4$ precipitation and dialyzed in 100 mM Tris-HCl, pH 8.0. In order to get rid of anti-GST antibodies, the IgG fraction was incubated with GST beads (Affigel 10, Bio-Rad) overnight at 4° C. The bound material was eluted with 4.5 M $MgCl_2$. The procedure was repeated with the unbound material several times, until no antibodies were eluted from GST beads. In order to get rid of antibodies against possible contamination of bacterial proteins, the same procedure was performed with immobilized heat-shocked E. coli lysate proteins.

The unbound material was then applied to I4-GST beads (Affigel 10, Bio-Rad), incubated 2 hr at room temperature or overnight at 4° C., and the bound material was eluted with 3.5 M $MgCl_2$. The eluted antibodies were dialyzed against 10 mM Tris-HCl, pH 8.0, and then against PBS, containing 0.025% $NaN_3$.

EXAMPLE 2

Elevation of A ChE Levels in CSF Upon CNS Stress

The inventors have found that ARP and ACHE-R are regulated following psychological, chemical, or physical insult to the CNS, at both the mRNA and enzyme levels. Examples of chemical insult include exposure to harmful substances such as nerve gas or insecticide. Examples of physical insult include head injury, head trauma, irradiation insult, and the like.

Using high-resolution in-situ hybridization (performed essentially as described in Experimental Procedures) to paraffin embedded human tumor sections, the inventors have found intensive overexpression of ACHE-R mRNA transcript in glioblastoma multiform tumors and particularly in their highly proliferative margins, as compared to the benign brain tissue surrounding these surgically removed tumors. Moreover, AChE-R expression levels increased considerably in post-surgery brain sections, especially following irradiation. Pathologically-classified tumor specimens further revealed pronounced increases in the extent and incidence of glioblastoma ACHE overproduction as related to tumor grading. These findings add to the general understanding of the molecular biology of glioblastoma tumors and can lead to novel, less harmful treatment paradigms.

The present inventors have also found, by in situ hybridization as described hereinabove, that ACHE-R mRNA changes its subcellular localization under stress. While under control conditions, said mRNA is detected exclusively in the soma of cortical neurons, following stress treatments ACHE-R mRNA extends into the proximal domain of dendrites. AChE expression was investigated in transgenic FVB/N mouse pedigrees expressing human ACHE splice variants. As controls, extracts of *Xeno laevis* oocytes expressing various human ACHE splice variants, were used. The transgenic mouse lines and *Xenopus* expression systems are described in Sternfeld et al., J. Physiol., Paris, 92, 249–55, 1998, which publication is incorporated herein in its entirety by reference. The influence of stress was investigated using the confined swim protocol for exerting acute psychological stress as detailed by Kaufer et al., Nature 393, 373–7, 1998.

Rabbit polyclonal antibodies against ARP (SEQ ID: No. 1) were obtained as described hereinabove. Antibodies against AChE common domain were obtained from a commercial supplier.

Figure 1:
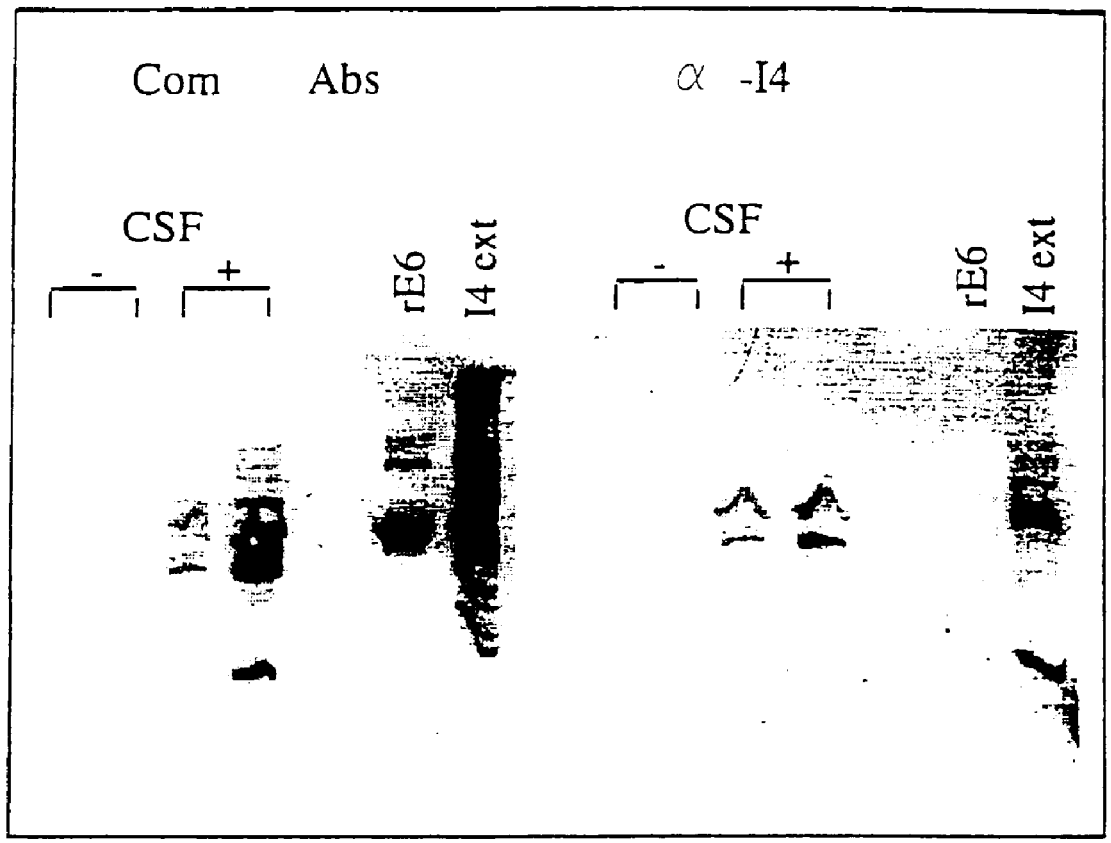
FIG. 1-AC*h*E expression in CSF under stress

Extracts of *Xenopus* oocytes or of mouse brain tissue (cortex or basal nuclei), or human cerebrospinal fluid (CSF), were subjected to SDS-PAGE. FIG. 1 shows immunoblots of cerebrospinal fluid (CSF), recombinant ACHE-S (rE6, Sigma), or ACHE-R (I4 extracts, produced in *Xenopus* oocytes as detailed hereinabove). The antibodies directed against the C-terminal peptide of ACHE-R, ARP (anti-I4, FIG. 1, right-hand side) fail to react with the ACHE-S protein, because the intron 4 region is spliced out in this mRNA. On the other hand, the antibodies clearly identify the ACHE-R protein. Antibodies raised against the common domain of ACHE (FIG. 1, left-hand side) are able to identify both ACHE-R and ACHE-S proteins.

In the following, "Non-stressed humans" refers to patients in which no enhanced Omnipaque signal was detected by CT brain scan, while "stressed humans" refers to patients in which an enhanced Omnipaque signal was detected by CT brain scan (see section hereinbelow relating to CT scans for details).

In cerebrospinal fluid of non-stressed humans (FIG. 1, "–"), no ACHE can be detected by either antibody. In contrast, both antibodies readily detect ACHE protein in the CSF of stressed human CSF (FIG. 1, "+"). The antibody against the common domain also detects a smaller fragment of ACHE (FIG. 1, left-hand side). This fragment corresponds in size to a C-terminally truncated ACHE-R protein. Indeed the antibody against the C-terminal peptide fails to detect this band (FIG. 1, left-hand side).

These experiments show that AChE occurs in increased levels in CSF upon CNS stress.

ACHE could also be detected in mouse brain tissue. FIG. 2 shows extracts from the cortex and basal nuclei region obtained from the brain of control and human ACHE transgenic mice. Transgenic FVB/N mouse pedigrees used herein, expressing human AChE variants, were described by Sternfeld et al., J. Physiol., Paris, 92, 249–55, 1998. E6 in FIG. 2 denotes a transgenic mouse expressing human ACHE-S, In is a transgenic mouse expressing insertion-inactivated human ACHE-S, I4$_{45}$ and I4$_{70}$A denote transgenic mice expressing various ACHE-R constructs. The tissues were extracted, run on SDS-PAGE gels and blotted as described in the above Sternfeld et al. As a control, extracts from *Xenopus* oocytes expressing human AChE-S (E6), ACHE-R (I4), or ACHE-E (E4) were run in parallel. FIG. 2A shows detection of human ACHE isoforms in transgenic mouse brain tissues by the antibody against the common domain of ACHE. ACHE is detected in cortex and basal nuclei. The transgenic mice expressing the insertion-inactivated ACHE-S construct (In), show weak expression of ACHE in basal nuclei, and fail to express ACHE over the level of control (non-transgenic) mice in cortex (FIG. 2A).

When using the anti-ARP antibodies, similar results were obtained, with the exception that no smaller fragments could be detected (FIG. 2B).

EXAMPLE 3

In vivo ARP Effects

ARP Accumulates in the Serum Under Stress

To find out whether the ARP peptide occurs naturally in blood and if its levels increase under psychological stress, FVB/N mice (n=12) were subjected to confined swim protocol for exerting acute psychological stress as detailed elsewhere (Kaufer et al., ibid). Serum samples removed 24 hr later were subjected to gradient gel electrophoresis. FIG. 3, top, shows a Poinceau-stained polyacrylamide gradient gel (4–20%, Bio-Rad) loaded with: (1) protein extract from COS cells transfected with ACHE-R encoding plasmid (Ben Aziz-Aloya et al., Proc. Natl. Acad. Sci. USA 90, 2471–5, 1993, Seidman et al., Mol. Cell. Biol. 15, 2993–3002, 1995) and mixed with synthetic ARP (ARP+ACHE-R); (2) recombinant ACHE-S (Sigma), mixed with synthetic ASP (ASP+ACHE-S); (3) serum (2 µL from a saline-injected mouse, removed 24 hr post-treatment (Control); (4) serum from a mouse subjected to confined-swim stress as described above, removed 24 hr post-treatment (Stress). Positions of molecular weight markers are shown on the left. The gel was then electroblotted and immunodetected (see "immunoblot" in the Experimental Procedures section for details) with affinity-purified rabbit antibodies elicited toward a recombinant GST-ARP fusion protein (FIG. 3, bottom). A 67 KDa protein, consistent with the expected size of ACHE-R, is detected in the serum (upper arrow). Furthermore, selective labeling of synthetic ARP (but not ACHE-S or ASP) by this antibody is detected. Accumulation of ARP in the serum of stressed mice is evident from the intense labeling of native ARP in the stressed mouse serum (lower arrow).

ARP Accumulation in the Serum Under Stress

The intense labeling of ARP in the unfractionated mouse serum removed 24 hr following stress treatment revealed more pronounced increases in this peptide than in its native protein ACHE-R This may reflect elevated proteolytic activity under stress. Combined with the absence of cleavage sites for common proteases within the ARP sequence, this further explains the reproducible series of proteolytic degradation products of serum ACHE-R which were intensified in the stressed serum samples. The physiological implications of this finding are that ACHE catalytic activity measurements are underestimates of the extent of its overproduction in the blood under stress. Likewise, measuring acetylcholine hydrolysis may underestimate the actual amounts of the ACHE protein and its degradation products in the brain or muscle. The reported decreases of AChE activity in Alzheimer's disease may hence mislead researchers and clinicians alike by masking the accumulation of morphologically active AChE-derived peptides with long-term effects.

EXAMPLE 4

ACHE-R effects on Hippocampal LTP Suggest Causal Involvement in Neuronal Stress Responses At the molecular level, psychological stress notably leads to fast yet long lasting modulation of gene expression. As for the genes concerning the cholinergic system, it has been shown that within one hour from acute stress, long lasting changes in cholinergic gene expression are facilitated (Kaufer et al., ibid. 1998). This particularly refers to drastic elevation in the levels of the normally rare "readthrough" variant of acetylcholinesterase (AChE-R), coupled with down-regulation of acetylcholine synthesizing and packaging proteins, the enzyme ChAT and the associated vesicular acetylcholine transporter (vAChT). This feedback response presumably contributes to reduce ACh levels following stress. Another outcome of stress responses involves a sudden increase in proteolytic activities. This leads, among other effects, to the cleavage of the C-terminal peptide (ARP=ACHE Readthrough Peptide) from the "readthrough" core enzyme. Immunodetection using anti-ARP antibodies reveals an increase in ACHE-R degradation products in the cerebrospinal fluid of patients under stress (Kaufer, PhD thesis, 2000). Moreover, injection of synthetic ARP by itself induces proliferation of hematopoietic progenitor cells and over-expression of bone marrow ACHE-R within 24 hr (Grisaru et al., submitted., 2000). These recent observations raised the intriguing possibility that ACHE-R also possesses physiological and behavioral functions. To test this working hypothesis, the effects on LTP of confined swim stress (1 hr after induction), was compared with those induced by transgenic mice over-expressing ACHE-R Differential Properties of AChE Variants in Synaptic Plasticity—Stress Effects The "readthrough" ACHE variant is the sole AChE variant that is up-regulated under psychological stress. Therefore, the possibility that the immediate recovery from psychological stress, in light of the over-expression of the AChE "readthrough" form will affect the pattern of LTP, was explored.

Stress was induced by forcing mice to swim twice for 4 min, with 4 min interval, and 1 hr later slices were taken for LTP experiments. The Schaffer collaterals-CA1 synapse pathway was tested. Basal field potentials were recorded for 15 min at 0.033 Hz. LTP was then induced by 3 consecutive tetanic stimulations, each of 1-sec duration, at 50 Hz with 20 sec inter-stimulus intervals. After tetanization, the change in the slope of the post-synaptic field potential (PSP) was followed for up to 3 hrs.

As shown in FIG. 4, while slices from control mice exhibit a stepwise potentiation of 235±27% (n=3), the slices from stressed mice demonstrate a different pattern. LTP had a slow onset delayed by 5 to 20 min and reached a plateau of 238±8% (n=8) potentiation, similar in that respect to control levels.

Therefore, stress changes the onset of LTP, lagging the early phase, yet achieving a subsequent stable potentiation.

AChE-R Effects

Transgenic mice over-expressing the "readthrough" isoform ACHE-R enabled direct examination of the question whether stress affects LTP, via elevation of ACHE-R Slices were prepared from adult control and transgenic mice, 3 to 5 months old, and LTP experiments were performed as described above.

As shown in FIG. 5, LTP in slices from transgenic mice over-expressing ACHE-R shows the same pattern of slow onset as in the stress-induced mice (compare to FIG. 4).

EXAMPLE 5

Disruption of the Blood-Brain Barrier is Associated with Stress Response

In a search for the molecular parameters associated with Blood-Brain-Barrier (BBB) disruption, a quantitative approach for analyzing human brain images derived by Computerized Tomography (CT), Magnetic Resonance Imaging (MRI), or Single Photon Emission CT (SPECT) was developed. FIG. 6B shows Computerized Tomography scans of patients with and without administration of Omnipaque (Nycomed AS), a soluble Iodine containing contrast agent. The Figure demonstrates that in normal patients, little contrast agent penetrates into the brain. However, in patients suffering from eclampsia during pregnancy, or in patients suffering focal epileptic seizures, a significantly enhanced penetrance of Omnipaque into the brain was found (see arrow in FIG. 6B). In 17 out of 34 patients with diverse CNS related symptoms, greater than 50% increase in brain penetration of the corresponding contrast agents, Omnipaque, gadolinium, or DTPA was observed.

FIG. 7A shows an example of enhanced Omnipaque signal revealed by CT scan versus control patients, also in post-ischemia patients.

When analyzing the above described data for the region of the brain showing greatest signal enhancement, significant signal enhancement was found in the Corona Radiata, gray matter, and soft tissue regions. Very little enhancement of penetration of contrast agent into the thalamus region was found, and the cerebellum and pons regions appeared unaffected. The percent enhancement of contrast agent signal was greatest (30% average) in the soft tissue (FIG. 7B).

These data indicate disruption of the BBB in patients with CNS pathologies. The data further show that disruption of CNS is associated with stress, and that the greatest extent of disruption of the BBB appears to occur in soft tissue, gray matter, and Corona Radiata regions.

In order to find out whether such disruption was linked to CNS stress, the signal enhancement (i.e., the percent increased penetrance of Omnipaque into the brain, as revealed by CT scan) was correlated to various stress parameters. FIG. 6C shows that disruption of the BBB was indeed correlated with stress indicators such as heart rate, leukocyte number, and serum cortisol levels. Blood pressure and body temperature, on the other hand, appeared not correlated to increased penetrance of contrast agents such as Omnipaque.

CSF samples taken from patients were run on SDS-PAGE gels, blotted, and stained with anti-AChE antibodies. The immunoblots revealed enhanced levels of ACHE-R in samples of stressed patients.

The above results were confirmed in animal experiments. Mice subjected to confined swim stress protocol as described above were injected with Evans Blue, a dye that usually does not penetrate the BBB because of its association with blood albumin. FIG. 6A shows that a large amount of the dye penetrates the brain of stressed mice, as compared to very low levels in nonstressed control mice.

EXAMPLE 6

Selective Increase in the A ChE-R Protein in the CSF of Alzheimer's Disease Patients To explore the potential involvement of specific acetylcholinesterase (ACHE) isoforms with Alzheimer's disease (AD), cerebrospinal fluid (CSF) samples from AD patients and matched controls were subjected to measurements of catalytic activities and to electrophoretic separation followed by immunoblot analyses and densitometric quantification of the labeling signals. As expected, and was shown previously, (Saez-Valero et al., J. Neurochem. 72, 1600–1608, 1999), AD CSF showed a lower ACHE activity (16.3+2.0 U/ml, n=6) than controls (28.3+4.9 U/ml, n=6). Data are mean ± SEM., One unit (U) is defined as the amount of enzyme hydrolyzing 1 nmol of acetylthiocholine per minute at 22° C. (not shown).

To test whether decrease in the AChE activity in AD CSF is related to differential expression of the ACHE-R, 8 μg protein from CSF samples were subjected to electrophoretic separation followed by immunoblot analysis and densitometric quantification. Blots were incubated with the antibody against the C-terminal peptide unique to ACHE-R (anti-ARP: top panel FIG. 8A), or with the antibody targeted to the common domain to all ACHE isoforms (anti-core; bottom panel).

As shown in FIG. 8A, three protein bands were observed between 66 and 46 kDa with both antibodies. These three protein bands probably reflect different extents of glycosylation of the ACHE proteins. However, the polyclonal antibody elicited towards the C-terminal peptide, unique to the stress associated "readthrough" AChE isoform, revealed a significant increase (p<0.05) in the AD CSF samples as compared with controls (top panel). On the other hand, when polyclonal antibody targeted to the N-terminal domain, common to all AChE isoforms, was used (bottom panel), no significant differences were found between AD and control samples, although the signal was stronger in control. Note that ARP, human recombinant AChE-S and AChE-R were used as positive or negative controls on right of the fillers.

The results were confirmed by quantitation of the blots using densitometric analysis (FIG. 8B).

Immunolabeling of ARP in Alzheimer's Disease vs. Normal Brain Sections

The pattern of expression of ACHE-R in brain sections of Alzheimer's disease patients was next investigated, in order to establish whether expression of this protein was a different also in the brain, similar to the differences in expression found in CSF.

FIGS. 9A to 9H present the immunolabeling with anti-ARP antibody in various paraffin embedded brain sections. Intriguingly, in Alzheimer's patients the anti-ARP stained mostly microglia, whereas in normal brain sections neurons and blood vessels were labeled. Indeed, considerable differences in labeling ARP in AD brain sections were found, compared to normal brain sections.

In conclusion, a selective increase in AChE-R protein occurs in CSF of AD patients. The more robust production of ACHE-R in AD could contribute to or attenuate the characteristic neurodeterioration of this form of dementia. In view of the non-cholinergic, non catalytic activities attribute to ACHE-R in modulating long-term neuronal reorganization following stress or other cholinergic insults (Kaufer et al., Nature 393, 373–377, 1998), this possibility seems quite probable.

The invention claimed is:

1. An antibody recognizing a C-terminal peptide derived from acetylcholinesterase said C-terminal peptide comprising the I4 peptide and denoted by SEQ ID No:1, for diagnosing central nervous system (CNS) stress.

2. The antibody according to claim 1, wherein the CNS stress is caused by any one of psychological, chemical and physical insult.

3. The antibody according to claim 1, which is monoclonal.

* * * * *